United States Patent
Namiki

(10) Patent No.: US 9,283,047 B2
(45) Date of Patent: Mar. 15, 2016

(54) CONTROL DEVICE AND CONTROL METHOD FOR SURGICAL SYSTEM

(71) Applicant: OLYMPUS CORPORATION, Tokyo (JP)

(72) Inventor: Hirotaka Namiki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 108 days.

(21) Appl. No.: 14/038,518

(22) Filed: Sep. 26, 2013

(65) Prior Publication Data

US 2014/0031838 A1 Jan. 30, 2014

Related U.S. Application Data

(63) Continuation of application No. PCT/JP2012/059129, filed on Mar. 28, 2012.

(30) Foreign Application Priority Data

Mar. 31, 2011 (JP) ................. 2011-079058

(51) Int. Cl.
*G05B 19/04* (2006.01)
*G05B 19/18* (2006.01)
*A61B 19/00* (2006.01)

(52) U.S. Cl.
CPC ..... *A61B 19/2203* (2013.01); *A61B 2019/2215* (2013.01); *A61B 2019/2223* (2013.01)

(58) Field of Classification Search
USPC .................. 606/1, 130; 128/898; 318/568.11; 600/117, 118, 104; 623/11.11; 700/264, 256, 258, 245, 257, 250
See application file for complete search history.

(56) References Cited

U.S. PATENT DOCUMENTS

| 4,853,874 | A | 8/1989 | Iwamoto et al. | |
|---|---|---|---|---|
| 5,855,583 | A | 1/1999 | Wang et al. | |
| 6,309,397 | B1 * | 10/2001 | Julian et al. | 606/130 |
| 6,645,196 | B1 * | 11/2003 | Nixon et al. | 606/1 |
| 7,373,219 | B2 | 5/2008 | Nowlin et al. | |
| 2002/0120254 | A1 * | 8/2002 | Julian et al. | 606/1 |

(Continued)

FOREIGN PATENT DOCUMENTS

| EP | 2 298 217 A2 | 3/2011 |
|---|---|---|
| JP | 63-150172 A | 6/1988 |

(Continued)

OTHER PUBLICATIONS

International Search Report dated May 22, 2012 issued in PCT/JP2012/059129.

(Continued)

*Primary Examiner* — Ronnie Mancho
(74) *Attorney, Agent, or Firm* — Scully, Scott, Murphy & Presser, PC

(57) ABSTRACT

A control device for surgical system that controls a surgical tool attached to a slave arm in accordance with manipulation input values for a position and an orientation from a remote control device, comprising a control unit that stores setting information for setting the position and the orientation of a first target portion of the surgical tool, corrects the manipulation input values in accordance with the setting information, and controls a position and an orientation of a post-correction second target portion of the surgical tool in compliance with corrected manipulation input values.

11 Claims, 10 Drawing Sheets

(56) References Cited

U.S. PATENT DOCUMENTS

| | | | |
|---|---|---|---|
| 2003/0158463 A1* | 8/2003 | Julian et al. | 600/104 |
| 2006/0276686 A1* | 12/2006 | Tsuji et al. | 600/117 |
| 2008/0046122 A1 | 2/2008 | Manzo et al. | |
| 2009/0062603 A1 | 3/2009 | Murakami et al. | |
| 2009/0112316 A1* | 4/2009 | Umemoto et al. | 623/11.11 |
| 2009/0143642 A1 | 6/2009 | Takahashi et al. | |
| 2011/0106141 A1* | 5/2011 | Nakamura | 606/205 |

FOREIGN PATENT DOCUMENTS

| | | |
|---|---|---|
| JP | 8-29509 B2 | 3/1996 |
| JP | H11-254354 A | 9/1999 |
| JP | 2001-204738 A | 7/2001 |
| JP | 2002-036155 A | 2/2002 |
| JP | 2004-17260 A | 1/2004 |
| JP | 2008-544814 A | 12/2008 |
| JP | 2009-061250 A | 3/2009 |
| JP | 2009-131374 A | 6/2009 |
| JP | 2010-82188 A | 4/2010 |
| WO | 2007/005555 A2 | 1/2007 |
| WO | WO 2009/123891 | 10/2009 |

OTHER PUBLICATIONS

Japanese Office Action dated Feb. 3, 2015 from related Japanese Patent Application No. 2011-079058, together with an English language translation.

Extended Supplementary European Search Report dated Mar. 27, 2015 from related European Application No. 12 76 3872.4.

* cited by examiner

CONTROL DEVICE AND CONTROL METHOD FOR SURGICAL SYSTEM

This application claims priority of and the benefit of Japanese Patent Application No. 2011-079058 filed on Mar. 31, 2011, and is a continuous application of international application PCT/JP2012/059129 filed on Mar. 28, 2012, the disclosures thereof are incorporated herein by reference.

BACKGROUND OF THE INVENTION

1. Field of the Invention

The present invention relates to a control device and a control method for a surgical system using a master-slave system.

2. Description of Related Art

Recently, research is being conducted into medical treatment performed by robots. In particular, in the field of surgery, various types of manipulation system that treat a patient using a manipulator with a multi-degree of freedom (multi-joint) arm have been proposed. One such manipulation system is a master-slave system that enables a manipulator for directly touching a body cavity of a patient (slave manipulator) to be manipulated by a remote control device. For example, in Japanese Published Unexamined Application No. S63-150172, a remote control device includes a master arm and a slave arm with different structures, and position information specified by the master arm is subjected to matrix conversion so as to enlarge or compress it before inputting it to the slave arm. Thus, even though the master arm and the slave arm are structured differently, it is possible to control the position of the distal end of the slave arm.

SUMMARY OF THE INVENTION

To achieve the above objects, a control device for surgical system according to a first aspect of the present invention controls a surgical tool attached to a slave arm in accordance with manipulation input values for a position and an orientation from a remote control device. The control device for surgical system includes a control unit that stores setting information for setting the position and the orientation of a first target portion of the surgical tool, corrects the manipulation input values in accordance with the setting information, and controls a position and an orientation of a post-correction second target portion of the surgical tool in compliance with corrected manipulation input values.

In the control device for surgical system of a second aspect of the present invention, in the first aspect, the control unit may perform an inverse kinematics computation to calculate a drive quantity for the slave arm needed to set the position and the orientation specified by the corrected manipulation input values.

In the control device for surgical system of a third aspect of the present invention, in the first aspect or the second aspect, the setting information may be information for correcting the manipulation input values such that the position and the orientation of the first target portion are changed from a reference position to a predetermined position determined for each of the surgical tools.

In the control device for surgical system of a fourth aspect of the present invention, in the third aspect, the surgical tool may include a grasping part for grasping an object, and the setting information may be information for correcting the manipulation input values such that the position and the orientation of the first target portion are changed from the reference position to a position on the grasping part that grasps the object.

In the control device for surgical system of a fifth aspect of the present invention, in the third aspect, the surgical tool may include an abutting part that abuts on an object and holds back the object, and the setting information may be information for correcting the manipulation input values such that the position and the orientation of the first target portion are changed from a reference position to a position on the abutting part that abuts on the object.

In the control device for surgical system of a sixth aspect of the present invention, in the third aspect, the surgical tool may include a cutting part that contacts an object and cuts the object; and the setting information may be information for correcting the manipulation input values such that the position and the orientation of the first target portion are changed from the reference position to a position on the cutting part that contacts the object.

In the control device for surgical system of a seventh aspect of the present invention, in any one of the first to the sixth aspects, the setting information may be information for correcting the manipulation input values such that the position and the orientation of the first target portion are changed from a reference position to a position of the surgical tool that accords with an individual variation of the user of the remote control device.

In the control device for surgical system of an eighth aspect of the present invention, in any one of the first to the seventh aspects, the control unit may correct the manipulation input values in compliance with the setting information that is different every time there is a change in a usage location of the surgical tool.

In the control device for surgical system of a ninth aspect of the present invention, in any one of the first to the eighth aspects, there may be further provided a display unit that displays the position and the orientation of the second target portion of the surgical tool.

In the control device for surgical system of a tenth aspect of the present invention, in any one of the first to the ninth aspects, the surgical tool may be provided with an indicator that indicates the position and the orientation of the second target portion.

Furthermore, to achieve the above objects, a control method for surgical system according to an eleventh aspect of the present invention controls a surgical tool attached to a slave arm in accordance with manipulation input values for a position and an orientation from a remote control device. The control method includes: storing setting information for setting the position and the orientation of a first target portion of the surgical tool, correcting the manipulation input values in accordance with the setting information, and controlling a position and an orientation of a post-correction second target portion of the surgical tool in compliance with corrected manipulation input values.

DETAILED DESCRIPTION OF THE INVENTION

An embodiment of the invention will be explained with reference to the drawings.

Figure 1:
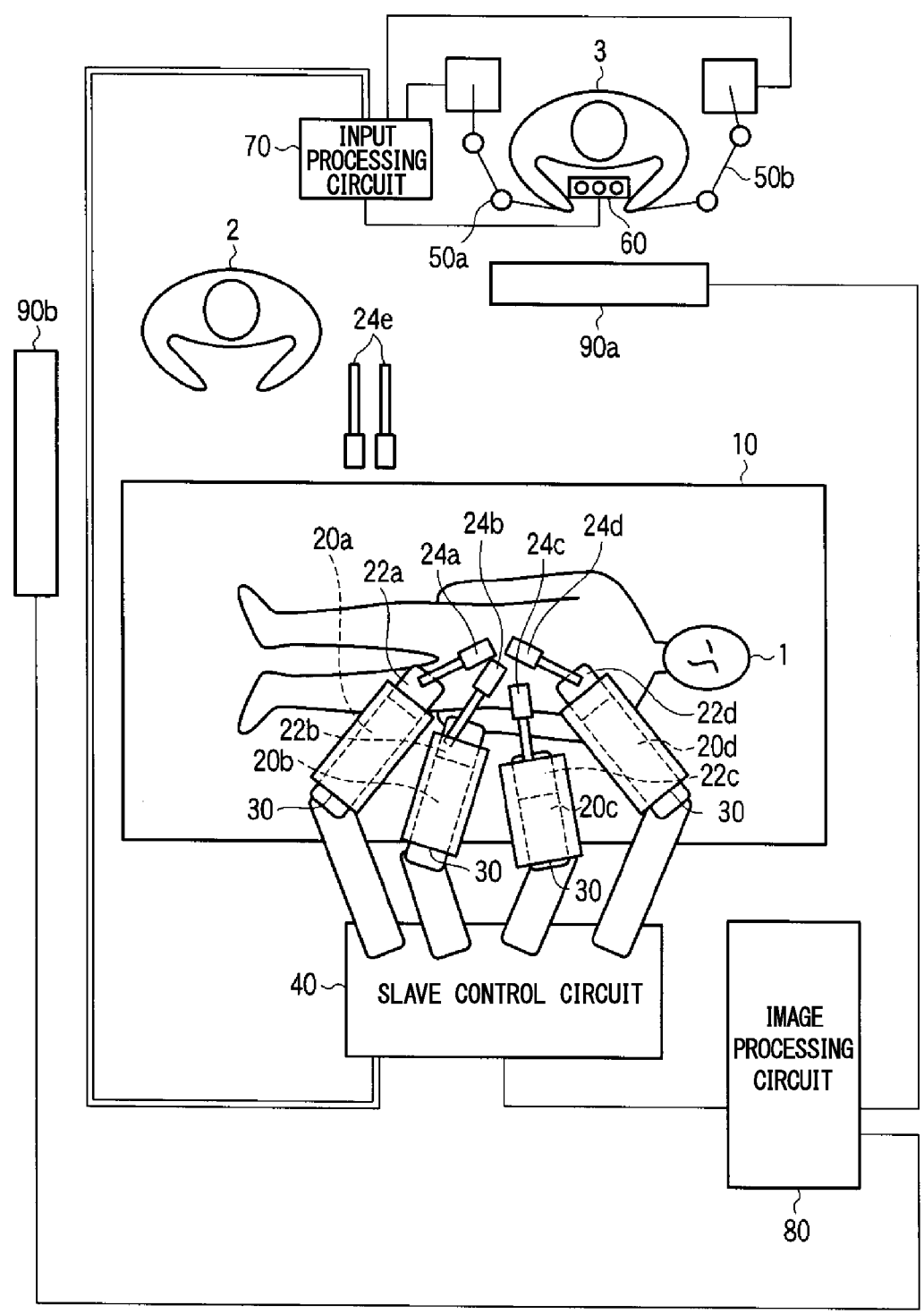
FIG. 1 is a diagram of the configuration of a surgical system according to an embodiment of the present invention.

FIG. 1 is a diagram of the configuration of a surgical system according to an embodiment of the present invention. The surgical system shown in FIG. 1 includes a surgical table 10, slave arms 20a to 20d, a slave control circuit (control unit) 40, master arms 50a and 50b, a manipulation unit 60, an input processing circuit 70, an image processing circuit 80, and displays 90a and 90b.

A patient 1, who is the object of observation and treatment, lies on the surgical table 10. The plurality of slave arms 20a, 20b, 20c, and 20d are installed near the surgical table 10. The slave arms 20a to 20d may be fitted to the surgical table 10. Each of the slave arms 20a, 20b, 20c, and 20d has multi-degree of freedom joints. By bending the joints of the slave arms 20a, 20b, 20c, and 20d, various types of surgical tools such as treatment tools and observation equipment attached to the distal-end side of the slave arms 20a to 20d are positioned with respect to the patient 1 lying on the surgical table 10. The distal-end side is the side facing the body cavity of the patient 1. The joints of the slave arms 20a to 20d are driven separately by power units provided inside the arms. As the power units, for example, a motor with a servo (a servo motor) mechanism including an encoder, a decelerator, and such like is used. The operation of the servo motors is controlled by the slave control circuit 40.

The slave arms 20a to 20d also include a plurality of power units for driving surgical tools 24a to 24d attached to the respective distal-end sides of the slave arms 20a to 20d. For example, servo motors are used as these power units. The operation of these servo motors is also controlled by the slave control circuit 40.

Power transmission adaptors for surgery (hereinafter simply 'adaptors') 22a, 22b, 22c, and 22d are provided between the slave arms 20a, 20b, 20c, and 20d and the surgical tools 24a, 24b, 24c, and 24d. The adaptors 22a, 22b, 22c, and 22d are thus respectively connected to the slave arms 20a, 20b, 20c, and 20d and to the surgical tools 24a, 24b, 24c, and 24d. The adaptors 22a to 22d are configured such that power generated in the power unit of the corresponding slave arm is transmitted to the corresponding surgical tool.

The surgical tools 24a to 24d have joints corresponding to multiple degrees of freedom, and are inserted into the body cavity of the patient 1 via an insertion hole (not shown) in the body wall of the patient 1. The distal-end parts of the surgical tools 24a to 24d can be driven so that they curve and rotate. The curve drive is performed by, for example, driving the servo motors provided inside each of the slave arms 20a to 20d such as to push and pull wire and rods inserted into each of the surgical tools 24a to 24d. The rotation drive is performed by, for example, driving the servo motors provided inside each of the slave arms 20a to 20d such as to operate rotation mechanisms inserted into each of the surgical tools 24a to 24d. Moreover, depending on the type of surgical tool, an open-close mechanism is provided at the distal-end of the surgical tool. This open-close mechanism is operated by, for example, driving the servo motors provided in each of the slave arms 20a to 20d such as to push and pull wire and rods inserted into the surgical tools.

For example, the slave arms 20a, 20b, and 20d are used as slave arms for treatment among the four slave arms 20a to 20d shown in FIG. 1. Various types of surgical operating tools are attached as the surgical tools 24a, 24b, and 24d to the slave arms for treatment 20a, 20b, and 20d. The surgical operating tools of this embodiment are tools for performing treatment and manipulations to a tissue portion inside the body of the patient 1, e.g. a grasping forceps, a needle-holder, a surgical scalpel, scissors, etc. The slave arm 20c is used as a camera arm for observation. Various types of observation tools are attached as the surgical tool 24c to the slave arm 20c. In this embodiment, observational equipment denotes a surgical tool for observing the tissue portion inside the body of the patient 1, such as an electronic endoscope.

The surgical tools 24a to 24d attached to the adaptors 22a to 22d can be replaced with a replacement tool 24e. The operation of replacing a tool can be performed by, for example, an assistant 2.

A drape 30 is for separating a part to be sterilized (hereinafter clean region) by a manipulator system for medical treatment from a part that is not sterilized (hereinafter unclean region). As shown in FIG. 1, the section of the power units of the slave arms 20a to 20d is covered by the drape 30 while surgery is being performed. By using the drape 30 to separate the clean region and the unclean region, they are prevented from being mixed after sterilization treatment. A minimum necessary range can be covered with the drape 30 as in FIG. 1, or, for example, the region up to the slave control circuit 40 can be covered with the drape 30.

The slave control circuit 40 includes, for example, a CPU, a memory, and such like. The slave control circuit 40 stores a predetermined program for controlling the slave arms 20a to 20d. The slave control circuit 40 of this embodiment also stores setting information for correcting a manipulation input value from the input processing circuit 70 when a change is made to the target portion whose position and orientation are to be controlled by the slave arms 20a, 20b, and 20d. This setting information will be explained in detail later.

In compliance with an input signal from the input processing circuit 70, the slave control circuit 40 controls the operations of the slave arms 20a to 20d and the surgical tools 24a to 24d. Based on the input signal from the input processing circuit 70, the slave control circuit 40 identifies a slave arm as a manipulation object of the master arm manipulated by a user 3. The slave control circuit 40 calculates the drive quantity for each joint of the slave arm needed to change the position and the orientation of the target portion determined in compliance with the type of surgical tool attached to the identified slave arm, the usage location of the surgical tool, and so on, to a second target value. Here, the second target value (second target position) is obtained by correcting the first target value (first target position) of the position and the orientation specified via the master arm. The drive quantity can be calculated by performing a conventional inverse kinematics computation. After calculating the drive quantity of each joint, the slave control circuit 40 controls each joint of the slave arm being manipulated by the master arm in accordance with the calculated drive quantity. When an input signal indicating a command to manipulate a grasping part or the like provided to the surgical tool is input to the slave control circuit 40 from the input processing circuit 70, the slave control circuit 40 controls the manipulation of the surgical tool in compliance with the input signal.

When an image signal from the observation device attached to the slave arm 20c is input, the slave control circuit 40 outputs the input image signal to the image processing circuit 80. The observation device and the image processing circuit can be linked together directly without inserting the slave control circuit 40 between them. The master arms 50a and 50b, which are examples of a remote control device, include a plurality of links. A position detector such as, for example, an encoder is provided to each link. Manipulation units for manipulating the surgical tools attached to the distal ends of the slave arms are provided at distal-end parts of the master arms 50a and 50b. The user 3 grasps the manipulation units while manipulating the master arms 50a and 50b. At this time, a detection signal indicating the manipulation quantity of each link of the master arms 50a and 50b is input from each position detector to the input processing circuit 70 as a signal corresponding to the target values for the position and the orientation of the target portion of the surgical tool.

In the example of FIG. 1, the user 3 manipulates the master arm 50a with his right hand and manipulates the master arm 50b with his left hand. FIG. 1 is an example where the two master arms 50a and 50b are used to manipulate four slave arms. In this case, the slave arms to be manipulated by the master arms must be switched as appropriate. For example, the user 3 can switch them by manipulating the manipulation unit 60. Of course, if the number of master arms is the same as the number of slave arms, so that they are in a one-to-one relationship, the switching operation is not needed. While this embodiment describes an arm having a plurality of links as an example of a remote control device, provided that the remote control device can make commands relating to position and orientation to the slave control circuit 40, it need not include links.

The manipulation unit 60 includes various types of manipulation members such as a switch button for switching the slave arms to be manipulated by the master arms 50a and 50b (hereinafter 'switch button'), a scaling change switch for changing the operation ratio of the master and the slaves, and a foot switch for stopping the system in the event of an emergency. When the user 3 has manipulated one of the manipulation members constituting the manipulation unit 60, a manipulation signal corresponding to the manipulation of that manipulation member is input from the manipulation unit 60 to the input processing circuit 70.

The input processing circuit 70 analyzes detection signals from the master arms 50a and 50b and a manipulation signal from the manipulation unit 60. In compliance with the result of the analysis of these signals, the input processing circuit 70 generates an input signal indicating target values for position and orientation. The input processing circuit 70 inputs this input signal indicating target values for position and orientation, and an input signal indicating the slave arms to be controlled, to the slave control circuit 40.

The image processing circuit 80 performs various types of image processing to display image signals input from the slave control circuit 40. This generates image data for display on a display for user 90a and a display for assistant 90b. The display for user 90a and the display for assistant 90b include, for example, liquid crystal displays, and display images based on image data generated by the image processing circuit 80 in compliance with the image signal obtained from the observation device. A two-dimensional image can easily be displayed, while a three-dimensional image can produce a sense of depth.

Subsequently, a way of thinking when changing the position of a target portion on a surgical tool that is controlled by the slave control circuit 40 functioning as one example of a control unit will be explained. In this embodiment, the slave control circuit 40 controls the position and the orientation of a target portion of the surgical tool that is considered optimal for each of various conditions such as the type of surgical tool attached to the slave arm and the usage location.

Firstly, in this embodiment, the position of the target portion of the surgical tool attached to the distal end of the slave arm whose position and orientation are to be controlled is changed in accordance with the purpose of that surgical tool. FIGS. 2A to 4B are explanatory diagrams to explain a way of thinking when changing the position in accordance with the type of the surgical tool. In this example, the target portion is a portion of the surgical tool that acts on the object of the surgery.

Figure 2A:
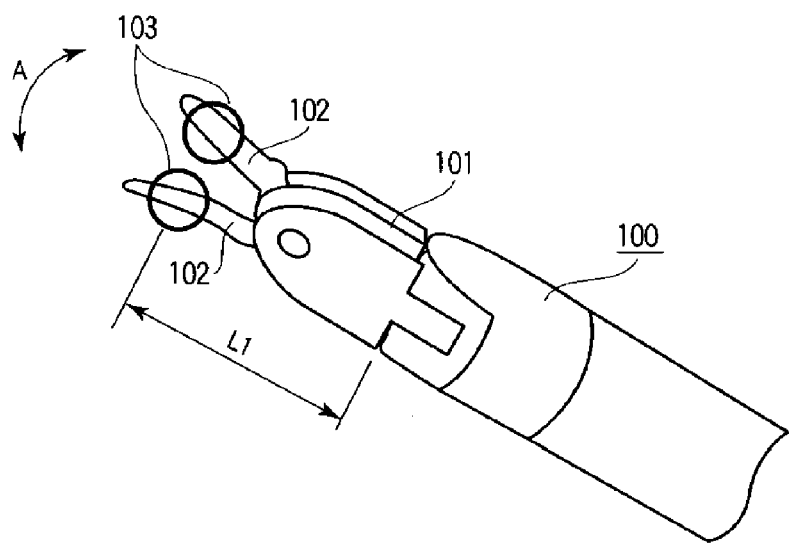
FIG. 2A is a diagram of a target portion of a surgical tool having the purpose of grasping an object.
Figure 2B:
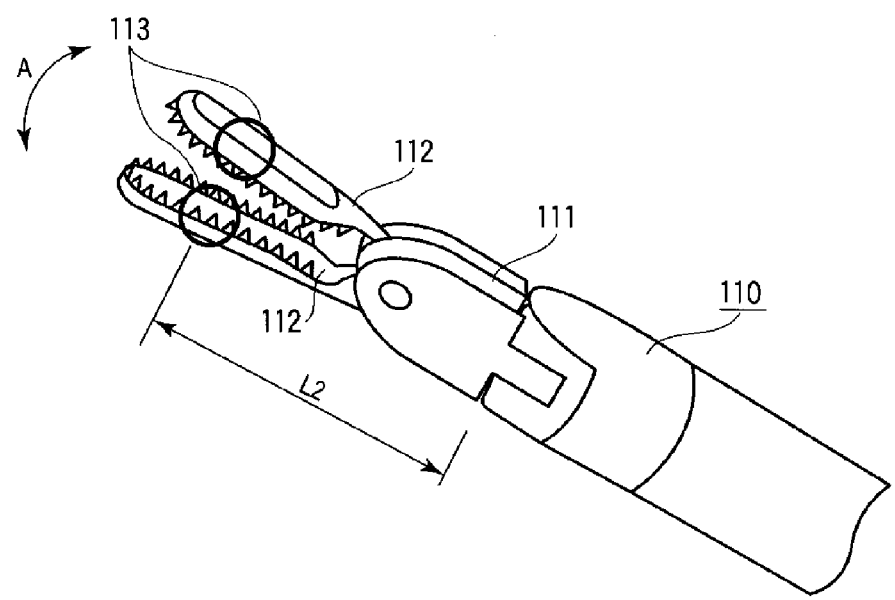
FIG. 2B is a diagram of a target portion of a surgical tool having the purpose of grasping an object.

FIGS. 2A and 2B are diagrams of target portions on a surgical tool having the purpose of 'grasping' the object. FIG. 2A is an example of a needle-holder 100. A needle-holder is a surgical tool for grasping a needle used for suturing an affected part or the like. FIG. 2B is an example of a grasping forceps 110. A grasping forceps is a surgical tool for grasping a blood vessel or the like. The explanation of FIGS. 2A and 2B similarly applies to various types of surgical tools having the purpose of 'grasping', other than those shown in FIGS. 2A and 2B.

The needle-holder 100 shown in FIG. 2A mainly includes a joint 101 and a grasping part 102. The joint 101 can rotate freely around a predetermined axis. While the joint shown in FIG. 2A is an example of a rotational joint, a linear driving joint that can move along a predetermined axis is also acceptable. The grasping part 102 includes a jaw part, which is attached to the joint 101 and can open and close in the indicated direction A. The jaw part forming this grasping part 102 opens and closes in compliance with the slave control circuit 40, and grasps the needle when closed.

The grasping forceps 110 shown in FIG. 2B mainly includes a joint 111 and a grasping part 112. The joint 111 can rotate freely around a predetermined axis. While the joint shown in FIG. 2B is an example of a rotational joint, a linear driving joint that can move along a predetermined axis is also acceptable. The grasping part 112 includes a jaw part, which is attached to the joint 111 and can open and close in the indicated A. The jaw part forming this grasping part 112 opens and closes in compliance with the slave control circuit 40, and grasps the object such as a blood vessel or the like when closed. The jaw part forming the grasping part 112 of grasping forceps 110 shown in FIG. 2B includes teeth, which enable it to grasp the object more reliably and securely.

When considering use of a surgical tool having the purpose of 'grasping' an object, such as those shown in FIG. 2A and FIG. 2B, in surgery, rather than controlling the position and the orientation of the joint 101 and the joint 111, it is more important for the user that he or she directly controls the position and the orientation of the portion that actually grasps the object. Therefore, in this embodiment, in regard to a surgical tool having the purpose of 'grasping' an object, such as those shown in FIG. 2A and FIG. 2B, the position of a target portion whose position and orientation are to be controlled is changed from the default position to the position of a center portion of the grasping part indicated by reference code 103 in FIG. 2A and reference code 113 in FIG. 2B. While here it is changed to the center portion of the grasping part, it need only be on the grasping part and does not need to be the center.

When the position of the target portion whose position and orientation are to be controlled has been changed, the manipulation input values from the input processing circuit 70 must be corrected accordingly. To correct them, setting information for correcting the manipulation input value is stored in the memory of the slave control circuit 40 of this embodiment. This setting information indicates the distance from the position of a predetermined reference target portion to the position of a target portion determined for each surgical tool. The reference target portion is, for example, the position of the joints (joint 101 and joint 111) of the surgical tools. The same goes for other surgical tools described later. When the positions of the joints are set as the reference target portions, a distance L1 shown in FIG. 2A is stored as setting information for the needle-holder 100, and a distance L2 shown in FIG. 2B is stored as setting information for the grasping forceps 110.

The position of the target portion of a specific surgical tool such as the needle-holder 100 can be set as the position of the reference target portion. For example, when the position indicated by the reference code 103 in FIG. 2A is the reference position, differential information indicating the distance between the position of the target portion set for each surgical tool and the position corresponding to the reference code 103 is stored as setting information of other surgical tools.

Figure 3A:
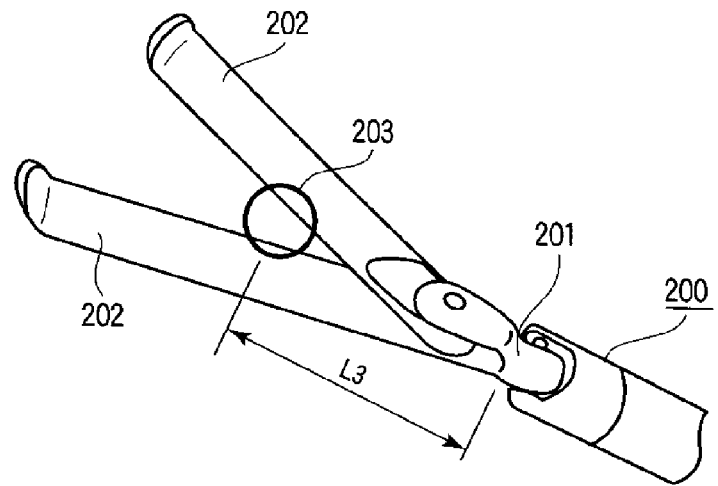
FIG. 3A is a diagram of a target portion of a surgical tool having the purpose of holding back an object.
Figure 3B:
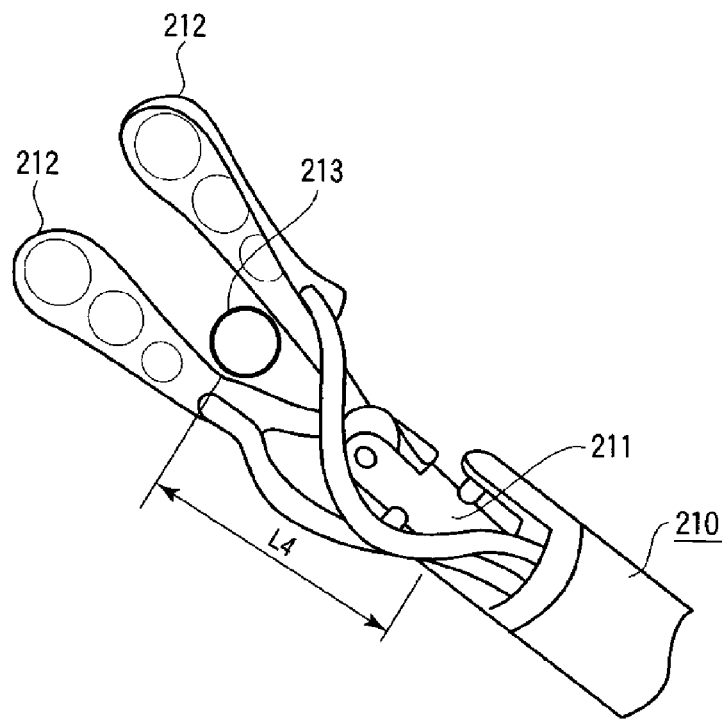
FIG. 3B is a diagram of a target portion of a surgical tool having the purpose of holding back an object.

FIGS. 3A and 3B are diagrams of a target portion on a surgical tool having the purpose of 'holding back' an object. FIG. 3A is an example of a retractor 200. The retractor 200 is a surgical tool for holding back and securing various types of objects. The retractor 200 is used to holding back objects such as internal organs that obstruct the field of vision needed for the surgery and thereby maintain that field of vision. FIG. 3B is an example of a stabilizer 210. The stabilizer 210 is a surgical tool for holding back the heart and thereby stabilizing the heartbeat. The following explanation relating to FIGS. 3A and 3B similarly applies to various types of surgical tools having the purpose of 'holding back' other than those shown in FIGS. 3A and 3B.

The retractor 200 shown in FIG. 3A mainly includes a joint 201 and an abutting part 202. The joint 201 can rotate freely around a predetermined axis. While the joint shown in FIG. 3A is an example of a rotational joint, a linear driving joint that can move along a predetermined axis is also acceptable. The abutting part 202 abuts on the object, and holds back and fixes the object. The abutting part 202 shown in FIG. 3A includes two thin plates that open and close freely, and these thin plates hold back the object. However, the abutting part 202 is not limited to this configuration.

The stabilizer 210 in FIG. 3B mainly includes a joint 211 and an abutting part 212. The joint 211 can rotate freely around a predetermined axis. While the joint shown in FIG. 3B is an example of a rotational joint, a linear driving joint that can move along a predetermined axis is also acceptable. The abutting part 212 holds back and secures an object by abutting against it.

When considering use of a surgical tool having the purpose of 'holding back' an object, such as those shown in FIGS. 3A and 3B, in surgery, rather than controlling the position and the orientation of the joint 201 and the joint 211, it is more important for the user that he or she directly controls the position and the orientation of the portion that actually holds back the object. Therefore, in this embodiment, in regard to a surgical tool having the purpose of 'holding back' an object, such as those shown in FIGS. 3A and 3B, the position of a target portion whose position and orientation are to be controlled is changed from the default position to a center-of-gravity position of an imaginary abutting part when it is assumed that there is an object to be held back by the abutting part indicated by reference code 203 in FIG. 3A and reference code 213 in FIG. 3B. This is actually a center position between the thin plates constituting the abutting part, though it need not be a center position.

When the position of the target portion whose position and orientation are to be controlled has been changed, the manipulation input values from the input processing circuit 70 must be corrected accordingly. To correct them, setting information for correcting the manipulation input value is stored in the memory of the slave control circuit 40 of this embodiment. A distance L3 shown in FIG. 3A is stored as setting information for the retractor 200, and a distance L4 shown in FIG. 3B is stored as setting information for the stabilizer 210.

Figure 4A:
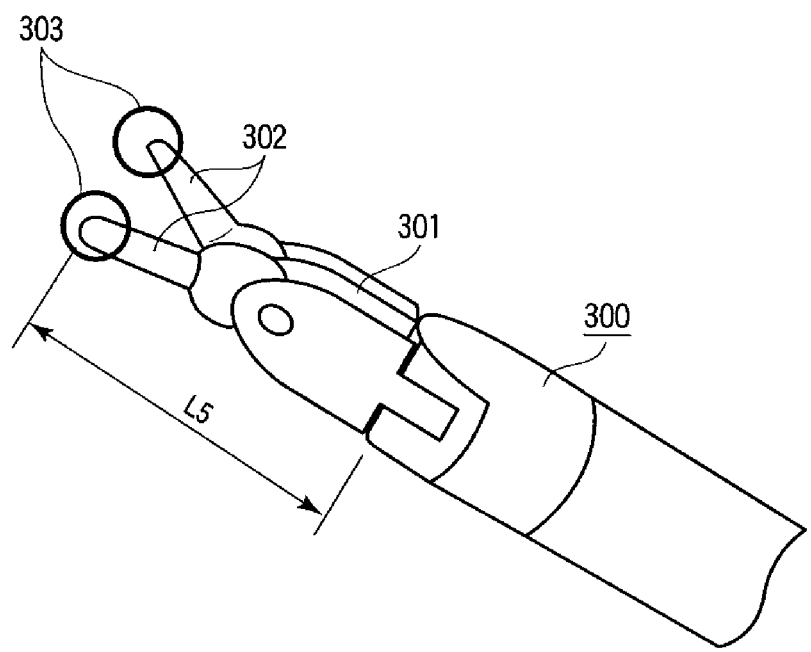
FIG. 4A is a diagram of an optimal target portion of a surgical tool having the purpose of cutting an object.
Figure 4B:
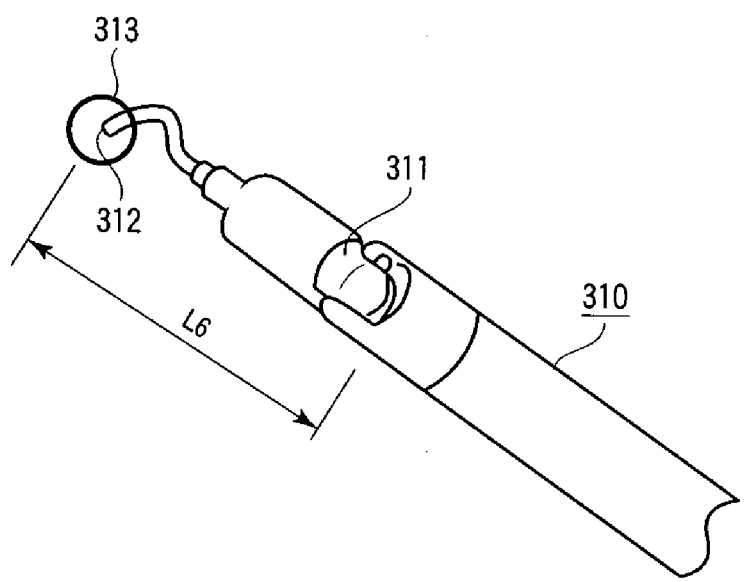
FIG. 4B is a diagram of an optimal target portion of a surgical tool having the purpose of cutting an object.

FIGS. 4A and 4B are diagrams of an optimal target portion of a surgical tool having the purpose of 'cutting' an object. FIG. 4A is an example of a pair of scissors 300. FIG. 4B is an example of an (electrical) scalpel 310. The following explanation relating to FIGS. 4A and 4B similarly applies to various types of surgical tools having the purpose of 'cutting' other than those shown in FIGS. 4A and 4B.

The scissors 300 shown in FIG. 4A mainly include a joint 301 and a cutting part 302. The joint 301 can rotate freely around a predetermined axis. While the joint shown in FIG. 4A is an example of a rotational joint, a linear driving joint that can move along a predetermined axis is also acceptable. The cutting part 302 includes two blades that open and close freely. These two blades clasp and cut the object.

The electric scalpel 310 in FIG. 4B mainly includes a joint 311 and a cutting part 312. The joint 311 can rotate freely around a predetermined axis. While the joint shown in FIG. 4B is an example of a rotational joint, a linear driving joint that can move along a predetermined axis is also acceptable. The cutting part 312 generates a high-frequency current at a distal-end part. The high-frequency current generated in this distal-end part cuts the object with Joule heat.

When considering use of a surgical tool having the purpose of 'cutting' an object, such as those shown in FIG. 4A and FIG. 4B, in surgery, rather than controlling the position and the orientation of the joint 301 and the joint 311, it is more important for the user that he or she directly controls the position and the orientation of the portion that actually cuts the object. Therefore, in this embodiment, in regard to a surgical tool having the purpose of 'cutting', such as those shown in FIG. 4A and FIG. 4B, the position of a target portion whose position and orientation are to be controlled is changed from the default position to a distal-end position indicated by reference code 303 in FIG. 4A and reference code 313 in FIG. 4B. It need not be changed to a distal-end position.

When the position of the target portion whose position and orientation are to be controlled has been changed, the manipulation input values from the input processing circuit 70 must be corrected accordingly. To correct them, setting information for correcting the manipulation input value is stored in the memory of the slave control circuit 40 of this embodiment. A distance L5 shown in FIG. 4A is stored as setting information for the scissors 300, and a distance L6 shown in FIG. 4B is stored as setting information for the electric scalpel 310.

Figure 5A:
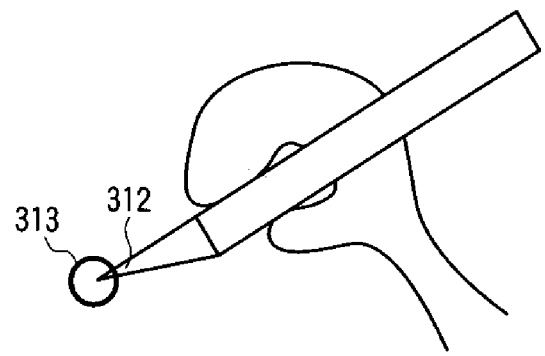
FIG. 5A is an explanatory diagram of a way of thinking when changing the position of a target portion in accordance with individual variation of a user.
Figure 5B:
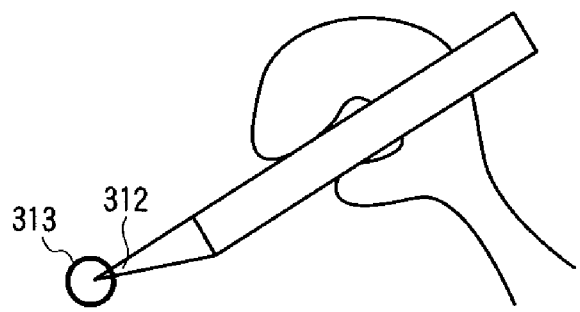
FIG. 5B is an explanatory diagram of a way of thinking when changing the position of a target portion in accordance with individual variation of a user.

In this embodiment, the position of the target portion on the surgical tool whose position and orientation are to be controlled is changed in accordance with the individual variation of the user 3 who is manipulating the master arm. FIGS. 5A and 5B are explanatory diagrams to explain a way of thinking when changing the position of the target portion in accordance with the individual variation of the user 3.

For example, when the user actually holds the scalpel and performs surgery, there are some users who hold the scalpel with a short grip as shown in FIG. 5A and some who hold it with a long grip as shown in FIG. 5B. These ways of holding the scalpel are the ones that the users deem optimal in consideration of their own preferences, the usage location, and such like. The same differences among users also apply when manipulating a master arm. For example, different users are liable to hold the same master arm manipulation unit in different ways. In the case of a scalpel, it is possible that different users will imagine different positions for the 'distal-end part' of cutting part 312. This embodiment enables the position of the target portion to be adjusted so as to reflect such differences among users. This adjustment is achieved by, for example, each user manually inputting adjustment information for adjusting the target portion. In compliance with the adjustment information that is input, the values of the setting information L1 to L6 mentioned above are changed for each user.

Figure 6A:
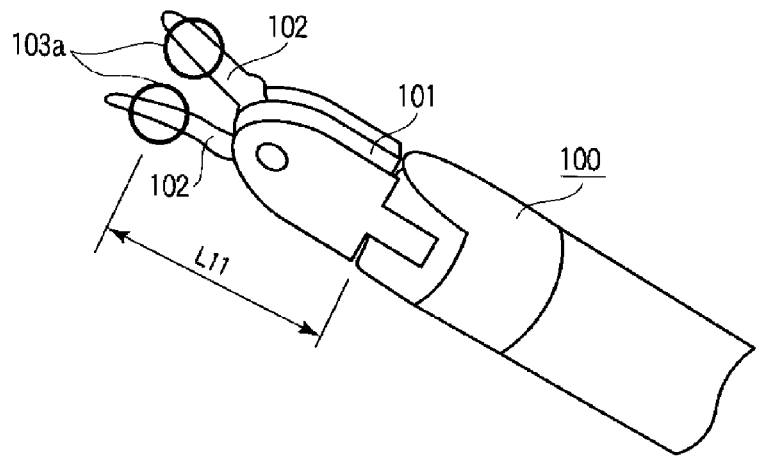
FIG. 6A is an explanatory diagram of a way of thinking when changing the position of a target portion in accordance with the usage location of a surgical tool.
Figure 6B:
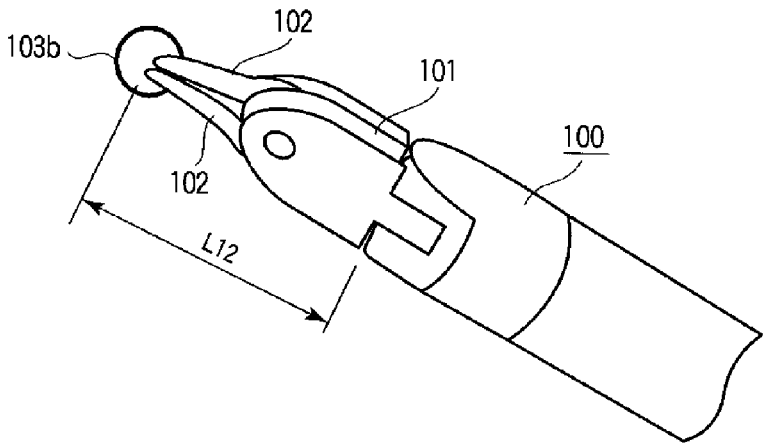
FIG. 6B is an explanatory diagram of a way of thinking when changing the position of a target portion in accordance with the usage location of a surgical tool.
Figure 6C:
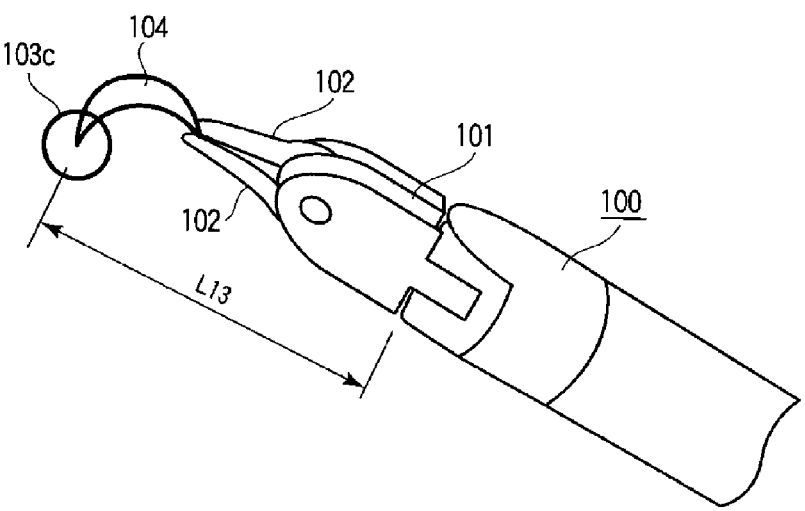
FIG. 6C is an explanatory diagram of a way of thinking when changing the position of a target portion in accordance with the usage location of a surgical tool.

Moreover, in this embodiment, the position of the target portion of the surgical tool whose position and orientation are to be controlled is changed in accordance with the usage location of the surgical tool when the master arm is being manipulated. FIGS. 6A to 6C are explanatory diagrams to explain a way of thinking when changing the position of the target portion in accordance with the usage location of the surgical tool.

Let us take the needle-holder 100 as an example. In the example of FIGS. 2A and 2B, the target portion of the needle-holder 100 is the portion 103a near the center of the grasping part 102 shown in FIG. 6A. This setting is particularly important while attempting to grasp a needle with the needle-holder 100. After the needle has been grasped, however, it must then be moved to the internal organ or the like that is to be sutured, and it is therefore preferable to control the position and the orientation of the grasping object, i.e. the position and the orientation of the distal-end portion 103b of the grasping part 102 shown in FIG. 6B than the position and orientation of the position 103a near the center. It is even more preferable to directly control the position and the orientation of the portion 103c of the needle 104 tip shown in FIG. 6C.

This kind of setting information for a target portion corresponding to the usage location of each surgical tool is stored in the slave control circuit 40. For example, a distance L11 (=L1) is stored as setting information for the location of FIG. 6A, a distance L12 is stored as setting information for the location of FIG. 6B, and a distance L13 is stored as setting information for the location of FIG. 6C.

Figure 7:
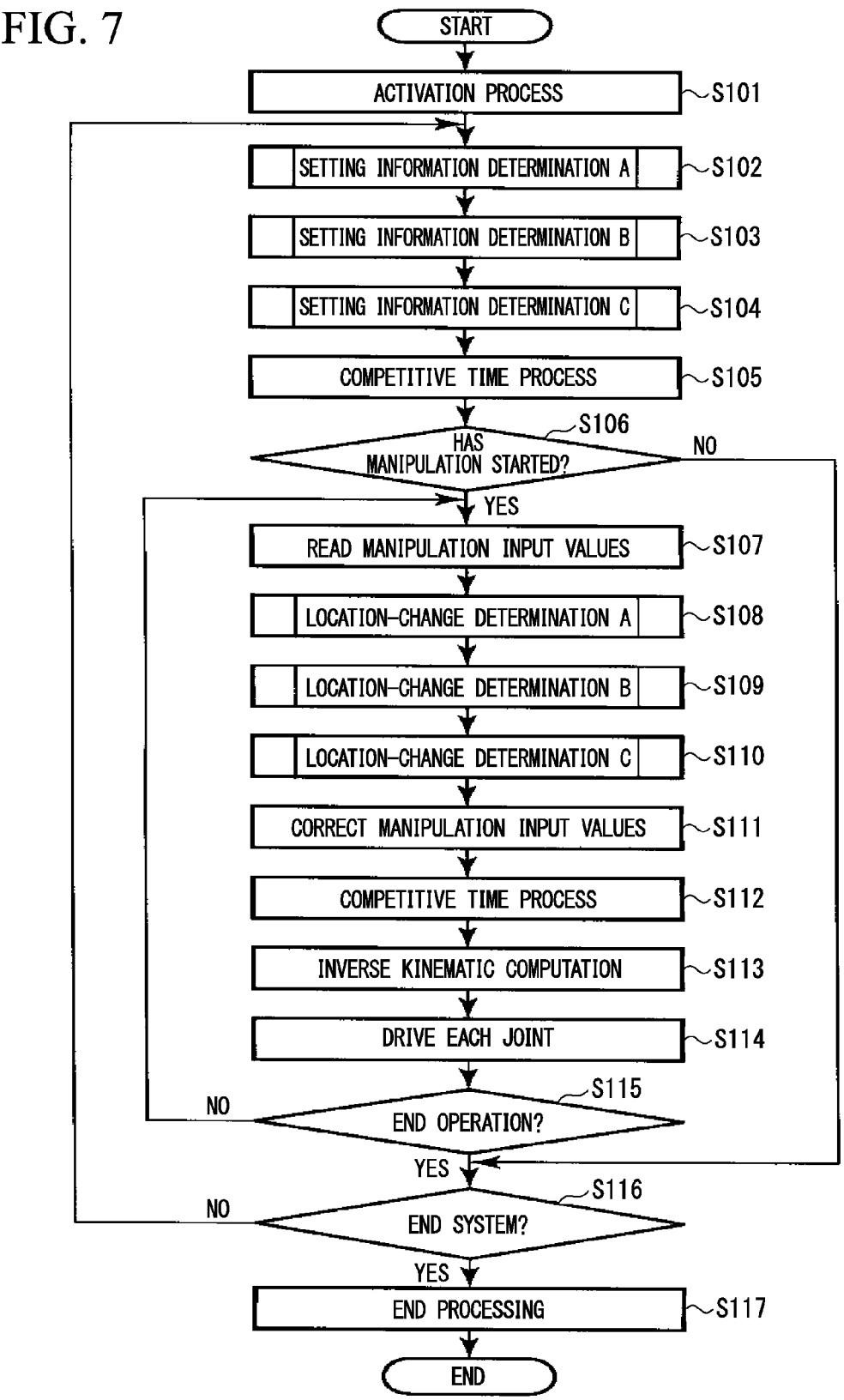
FIG. 7 is a flowchart of a main operation of a surgical system according to this embodiment including a process of changing a target portion.

FIG. 7 is a flowchart of a main operation of a surgical system according to this embodiment including a process of changing the target portion as described above. The processes of the flowchart shown in FIG. 7 are executed by, for example, the slave control circuit 40. After the surgical system is turned on, the slave control circuit 40 executes an activation process for activating each block of the surgical system (Step S101). In this activation process, the slave control circuit 40 executes an initialization process of the positions of the master arms 50a and 50b, an initialization process of the positions of the slave arms 20a to 20d, an initialization process of various set values to be used in the slave control circuit 40, etc. Information relating to the user 3 can be input to the slave control circuit 40 during this activation process. For example, the user 3 can manually input this information of the users 3. In addition, information can be input by utilizing both ID card authentication and fingerprint authentication. During the activation process, it is also possible to input adjustment information for adjusting the position of the target portion to the slave control circuit 40. For example, the user 3 can manually input this information of the user 3.

After the activation process, the slave control circuit 40 executes a setting information determination process A (Step S102). The slave control circuit 40 then executes a setting information determination process B (Step S103). The slave control circuit 40 then executes a setting information determination process C (Step S104). The sequence of executing the setting information determination processes A, B, and C can be changed as appropriate. Also, the setting information determination processes A, B, and C can be omitted as appropriate.

The setting information determination processes will be explained.

Figure 8:
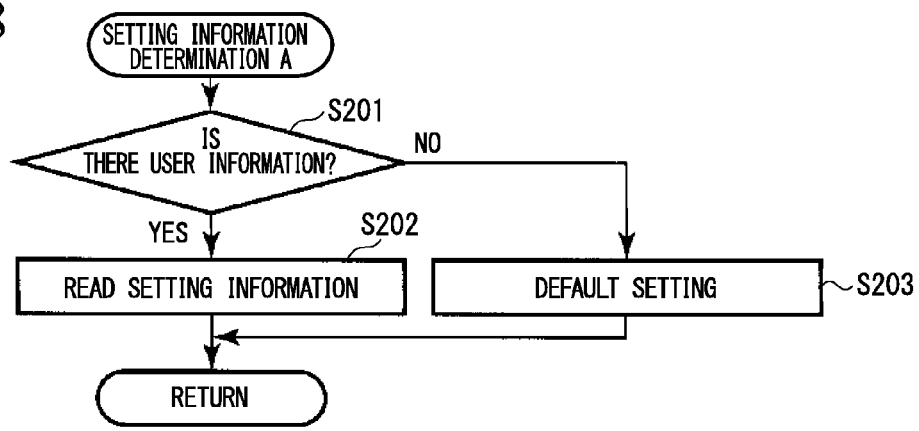
FIG. 8 is a detailed flowchart of a setting information determination process A.

FIG. 8 is a detailed flowchart of the setting information determination process A. In FIG. 8, the slave control circuit 40 determines whether user information has been input (Step S201). In the determination of Step S201, if user information has been input, the slave control circuit 40 reads the setting information corresponding to the user specified in that user information from the memory (Step S202). This setting information is for correcting the target portion in accordance with the individual variation of the user 3 such as that shown in FIGS. 5A and 5B. After reading the setting information, the slave control circuit 40 ends the processes of FIG. 8 and executes the processes from Step S103 in FIG. 7.

In the determination of Step S201, if the user information has not been input, the slave control circuit 40 does not use the setting information corresponding to the user, and instead uses the default setting information (Step S203). In this case, the slave control circuit 40 ends the processes of FIG. 8 and executes the processes from Step S103 in FIG. 7. When using the default setting information, a manipulation signal (explained below) is not corrected. In this case, the reference target portion position becomes the position of the target portion.

Figure 9:
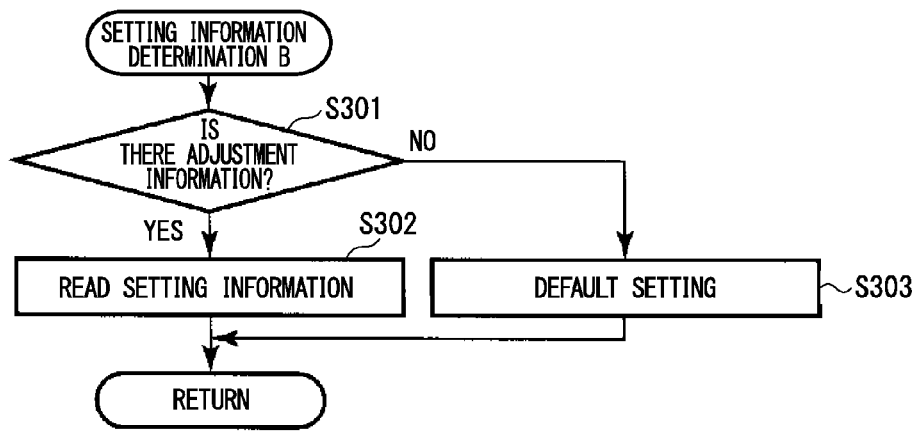
FIG. 9 is a detailed flowchart of a setting information determination process B.

FIG. 9 is a detailed flowchart of the setting information determination process B. In FIG. 9, the slave control circuit 40 determines whether adjustment information has been input (Step S301). In the determination of Step S301, if adjustment information has been input, the slave control circuit 40 reads the setting information corresponding to that adjustment information from the memory (Step S302). After reading the setting information, the slave control circuit 40 ends the processes of FIG. 9 and executes the processes from Step S104 in FIG. 7.

In the determination of Step S301, if adjustment information has not been input, the slave control circuit 40 does not use the setting information corresponding to the adjustment information, and instead uses the default setting information (Step S303). In this case, the slave control circuit 40 ends the processes of FIG. 9 and executes the processes from Step S104 in FIG. 7.

Figure 10:
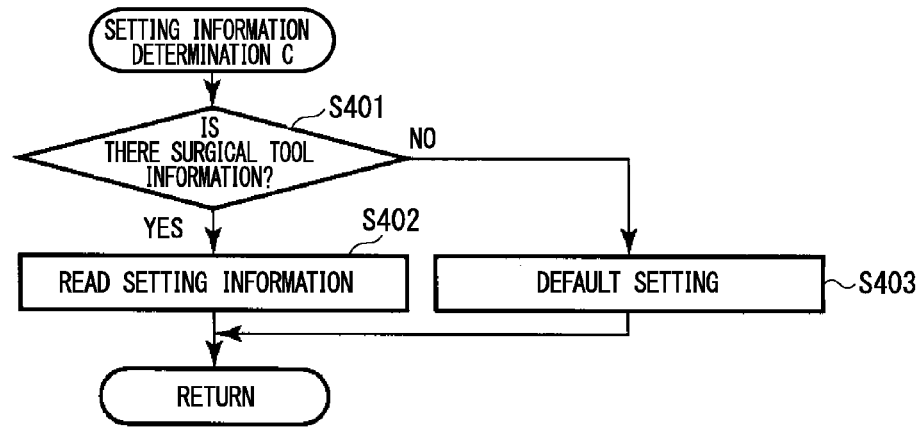
FIG. 10 is a detailed flowchart of a setting information determination process C.

FIG. 10 is a detailed flowchart of the setting information determination process C. In FIG. 10, the slave control circuit 40 determines whether surgical tool information has been input (Step S401). Surgical tool information indicates the type of the surgical tool attached to each slave arm. Here, when the surgical tool is electrically connected to the slave arm, the surgical tool information can be obtained directly from the surgical tool. In this case, a memory or the like is provided for storing the surgical tool information in the surgical tool. The user 3 may be able to input the surgical tool information manually. In the determination of Step S401, if surgical tool information has been input, the slave control circuit 40 reads the setting information corresponding to that surgical tool indicated by the surgical tool information from the memory (Step S402). This setting information is for correcting the target portion in accordance with the type (purpose) of the surgical tool, such as that shown in FIGS. 2A to 4B. After reading the setting information, the slave control circuit 40 ends the processes of FIG. 10 and executes the processes from Step S105 in FIG. 7.

In the determination of Step S401, if surgical tool information has not been input, the slave control circuit 40 does not use the setting information corresponding to the surgical tool, and instead uses the default setting information (Step S403). In this case, the slave control circuit 40 ends the processes of FIG. 10 and executes the processes from Step S105 in FIG. 7.

The explanation will now return to FIG. 7. After executing the various setting information determination processes shown in FIGS. 8 to 10, the slave control circuit 40 executes a competitive time process with respect to the setting information determination process (Step S105). A competitive time process reduces a plurality of pieces of setting information that have been read to a single piece of setting information. For example, the setting information read in the setting information determination process A corresponds to the present user 3, and may contain a setting for the target portion of each surgical tool. Therefore, when the setting information read in the setting information determination process A also contains a setting for each surgical tool, priority is given to the setting information read in the setting information determination process A, and the setting information read in the setting information determination process C is, for example, invalidated. In contrast, the setting information read in the setting information determination process B is for finely adjusting the target portion. Therefore, when setting information is read in the setting information determination process B, setting information that was read in another setting information determination process is corrected in compliance with the setting information read in the setting information determination process B. While this example is uses prioritization, it is acceptable to determine an average value of the plurality of pieces of setting information.

After the competitive time process of Step S105, the slave control circuit 40 determines whether a manipulation of the surgical system has started from, for example, the output of the input processing circuit 70 (Step S106). For example, when a manipulation input value has been input as an input signal from the input processing circuit 70, the slave control circuit 40 determines that a manipulation of the surgical system has started.

In the determination of Step S106, when a manipulation of the surgical system has started, the slave control circuit 40 reads the manipulation input value that was input (Step S107). The slave control circuit 40 then executes a location-change determination process A (Step S108). The slave control circuit 40 then executes a location-change determination process B (Step S109), and then executes a location-change determination process C (Step S110). The sequence of executing the location-change determination processes A, B, and C can be changed as appropriate. Also, the location-change determination processes A, B, and C can be omitted as appropriate.

The location-change determination processes will be explained. The example below describes a location-change determination process when the surgical tool is one having the purpose of 'grasping'. For other types of surgical tools, the contents of the determinations in Steps S501, S601, and S701 described below can be designed accordingly for those tools.

Figure 11:
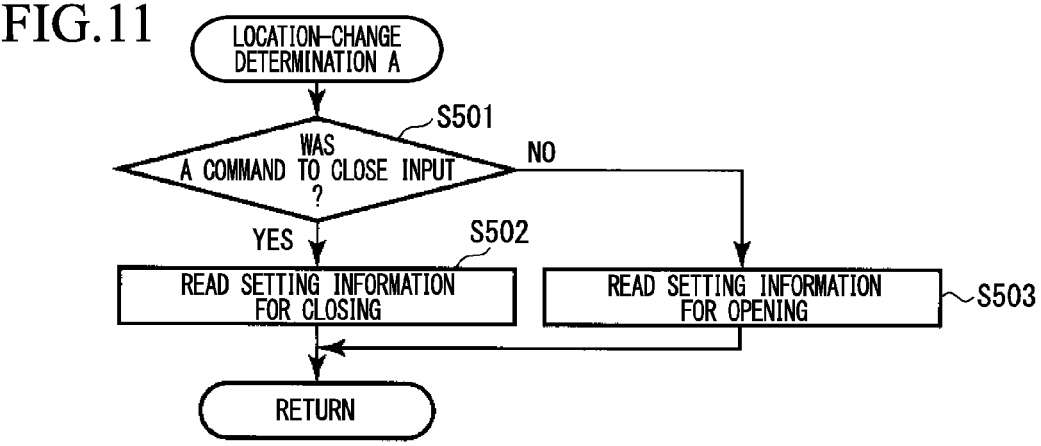
FIG. 11 is a detailed flowchart of a location-change determination process A.

FIG. 11 is a detailed flowchart of the location-change determination process A. In FIG. 11, the slave control circuit 40 determines, based on the manipulation input value read from the input processing circuit 70, whether it has been commanded to close the grasping part of the surgical tool (Step S501). In the determination of Step S501, when it has been commanded to close the grasping part of the surgical tool, the slave control circuit 40 reads the setting information corresponding to a case where the grasping part is closed from the memory (Step S502). This setting information corresponds to a location such as that shown in FIG. 6B. After reading the setting information, the slave control circuit 40 ends the processes of FIG. 11 and executes the processes from Step S109 in FIG. 7.

In the determination of Step S501, when it has not been commanded to close the grasping part of the surgical tool, the slave control circuit 40 reads setting information corresponding to a case where the grasping part is not closed from the memory (Step S503). This setting information corresponds to a location such as that shown in FIG. 6A. After reading the setting information, the slave control circuit 40 ends the processes of FIG. 11 and executes the processes from Step S109 in FIG. 7.

Figure 12:
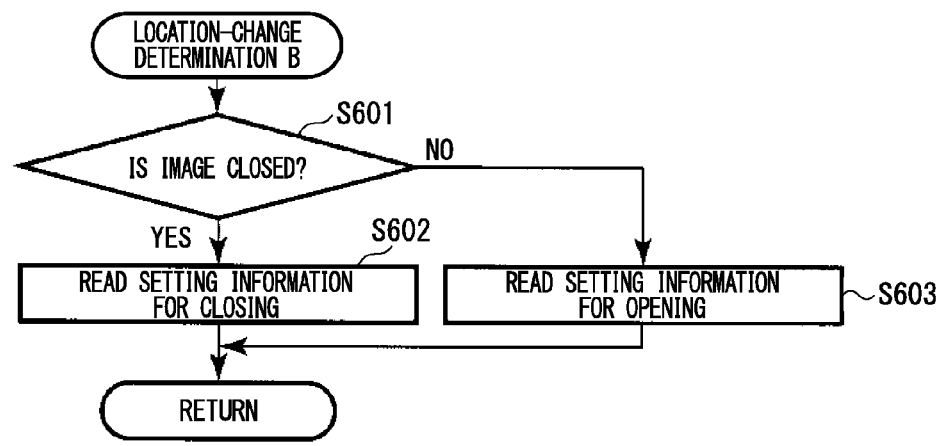
FIG. 12 is a detailed flowchart of a location-change determination process B.

FIG. 12 is a detailed flowchart of the location-change determination process B. While the location-change determination process B determines the same location-change as the location-change determination process A, its determination procedure is different. In FIG. 12, the slave control circuit 40 determines whether the grasping part of the surgical tool is closed from an image of the surgical tool vicinity obtained from the image processing circuit 80 (Step S601). This determination can be performed by, for example, template matching. That is, a template image of the grasping part in a closed state is stored in the memory, and, when the slave control circuit 40 determines that the image obtained from the image processing circuit 80 substantially matches the template image, it determines that the grasping part is closed. In the determination of Step S601, when the slave control circuit 40 has been commanded to close the grasping part of the surgical tool, it reads the setting information corresponding to a case where the grasping part is closed from the memory (Step S602). In determining the setting information, when setting information is read for every surgical tool and every user, the slave control circuit 40 reads setting information for a case where the grasping part is closed corresponding to the setting information that was read. The same goes for the subsequent location-change determination processes. After reading the setting information, the slave control circuit 40 ends the processes of FIG. 12 and executes the processes from Step S110 in FIG. 7.

When the slave control circuit 40 determines in Step S601 that the grasping part is not closed, it reads setting information corresponding to a case where the grasping part is not closed from the memory (Step S603). This setting information corresponds to a location such as that shown in FIG. 6A. After reading the setting information, the slave control circuit 40 ends the processes of FIG. 12 and executes the processes from Step S110 in FIG. 7.

Figure 13:
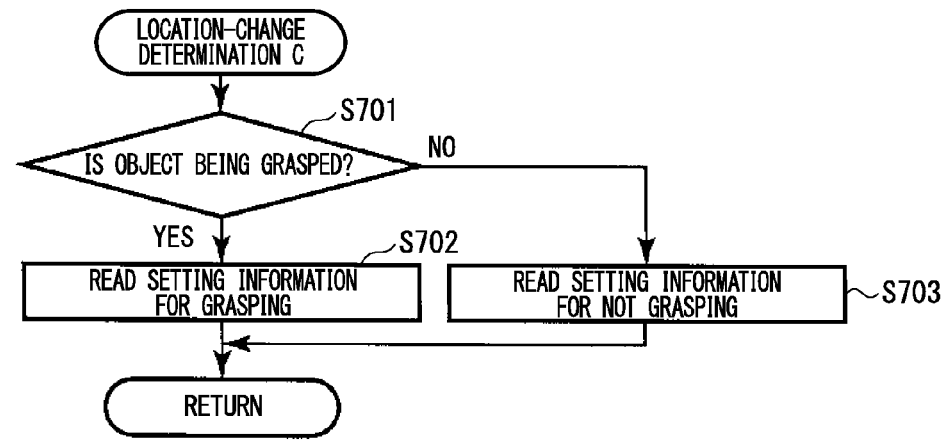
FIG. 13 is a detailed flowchart of a location-change determination process C.

FIG. 13 is a detailed flowchart of the location-change determination process C. In FIG. 13, the slave control circuit 40 determines whether the grasping part of the surgical tool is grasping some sort of object, based on an image of the surgical tool vicinity obtained from the image processing circuit 80 (Step S701). This determination can be performed by, for example, template matching. That is, when the slave control circuit 40 determines that a known object such as a needle is between the jaws constituting the grasping part, it determines that the grasping part is grasping the object. In the determination of Step S701, when the grasping part is grasping the object, the slave control circuit 40 reads the setting information corresponding to a case where the grasping part is grasping an object from the memory (Step S702). This setting information corresponds to a location such as that shown in FIG. 6C. After reading the setting information, the slave control circuit 40 ends the processes of FIG. 13 and executes the processes from Step S111 in FIG. 7.

When the grasping part of the surgical tool is not grasping a known object such as a needle, the slave control circuit 40 reads setting information corresponding to a case where the grasping part is not grasping an object from the memory (Step S703). This setting information corresponds to one of the locations shown in FIG. 6A and FIG. 6B. After reading the setting information, the slave control circuit 40 ends the processes of FIG. 13 and executes the processes from Step S111 in FIG. 7.

The explanation now returns to FIG. 7. After performing the location-change determination processes shown in FIGS. 11 to 13, the slave control circuit 40 corrects the manipulation input value in compliance with the setting information that was read (Step S111). For example, the post-correction manipulation input value (corrected manipulation input value) is obtained by adding the setting information read as the result of the setting information determination, and the setting information read as the result of the location-change determination, to the pre-correction manipulation input value (the manipulation input value read in Step S107).

Distance information from the reference target portion used as setting information is actually distance information in a three-dimensional space. In this case, when the orientation of the surgical tool has changed, the direction of a post-correction target portion (second target portion) with respect to the reference target portion (first target portion) changes in accordance with that change in the orientation. The setting information must therefore be converted in accordance with the change in the orientation of the surgical tool. For example, when the manipulation input value has six degrees of freedom (three degrees of freedom for position and three degrees of freedom for orientation), and when the post-correction target portion is at an X-axis position with respect to the reference target portion, the distance information is added as setting information to the X component of the manipulation input value.

After correcting the manipulation input value, the slave control circuit 40 executes a competitive time process (Step S112). For example, when the setting information was read as a result of only one of a setting information determination and a location-change determination, that setting information is used. When setting information was read from both, the setting information read as the result of the location-change determination process is used. This setting information is obtained by correcting the setting information that was read as a result of the setting information determination process.

The slave control circuit 40 then performs an inverse kinematic computation to calculate the drive quantity of each joint of the slave arm needed to change the post-correction position and orientation of the target portion to the position and the orientation specified by the post-correction manipulation input value (Step S113). Since inverse kinematic computation is a conventionally known technique, it will not be explained here. The slave control circuit 40 then drives each joint of the slave arm in compliance with the calculated drive quantity (Step S114). If a command to open/close the surgical tool or the like has been made, the slave control circuit 40 also drives the surgical tool.

The slave control circuit 40 then determines from, for example, the output of the input processing circuit 70, whether the manipulation of the surgical system has ended (Step S115). For example, when an manipulation input value is not input as an input signal from the input processing circuit 70 for a predetermined time, the slave control circuit 40 determines that the manipulation of the surgical system has ended. In the determination of Step S115, when the manipulation of the surgical system has not ended, the slave control circuit 40 returns the process to Step S107 and reads the next manipulation input value.

On the other hand, in the determination of Step S115, when the manipulation of the surgical system has ended, the slave control circuit 40 determines whether to end the operation of this surgical system (Step S116). For example, when power of the surgical system has been turned off or the foot switch has been turned on, the slave control circuit 40 determines to end the operation of the system. In the determination of Step S116, when the slave control circuit 40 determines not to end the operation of the surgical system, it returns to Step S102 and re-executes the processes from the setting information determination process A. Various changes, such as switching to a new user and replacing the surgical tools, are performed while the system is turned off and not operating. In the determination of Step S116, when the slave control circuit 40 determines to end the operation of the surgical system, it performs an end process and then ends the processes of FIG. 7 (Step S117).

As described above, according to this embodiment, in a surgical system using a master-slave method, the target portion whose position and orientation are to be controlled by the slave arm is changed in accordance with various conditions such as a change in the usage location of the surgical tool, for each user and for each surgical tool. This can enhance the manipulability.

In this embodiment, the remote control device includes the manipulation device (including the manipulation unit and the master arms) which stands away from the slave arms. When the manipulation device does not include the master arms, it may be attached to the slave arms or the surgical tool. That is, the device, which stands away from an end effector of the grasping part or the like and manipulates the manipulation device, is referred to as the remote control device.

Figure 14:
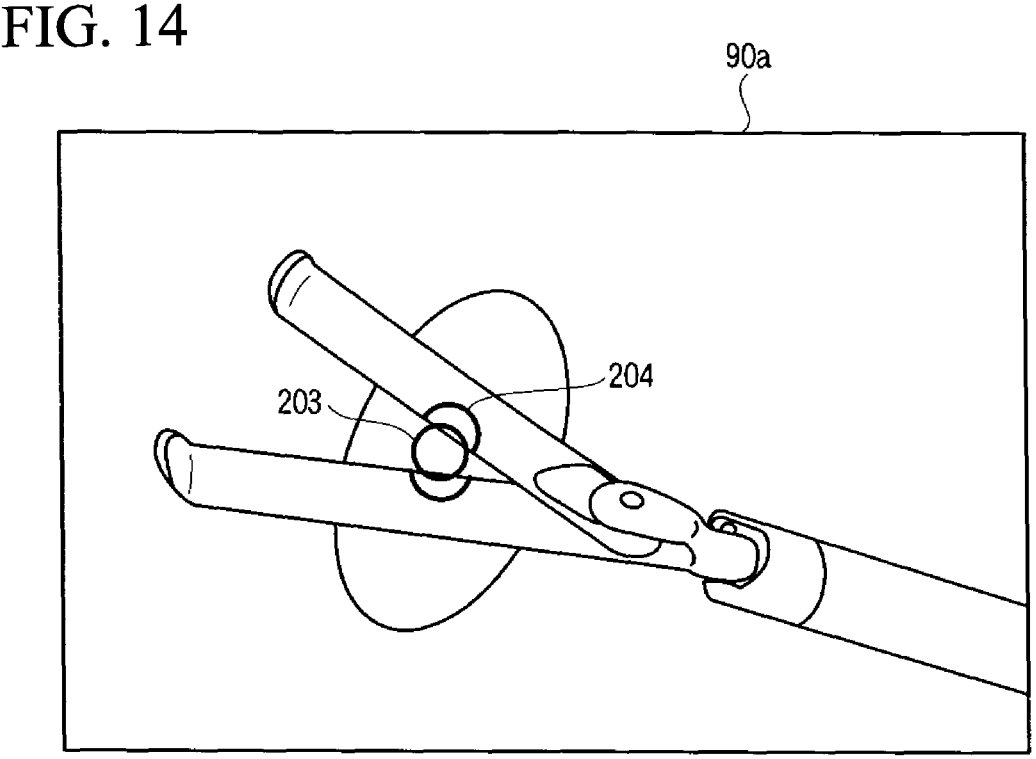
FIG. 14 is a diagram of a modification that provides an overlay display of an indicator indicating a target portion.

When changing the target portion in accordance with a location change, there is a possibility that the user will be confused about which portion is the present target portion. Accordingly, as shown in FIG. 14, an indicator 203 indicating the present target portion is overlaid on the image displayed on the display for user 90a. An indicator 204 can also be provided on the surgical tool itself. Such an indicator 204 can also serve as a mark when determining from the above image whether the surgical tool is open or closed. Moreover, that determination can be made by detecting the edge of the tool. Since there is a possibility that the surgical tool will be concealed by internal organs, blood, and the like, the determination is preferably made by detecting a plurality of points on the edge.

It is not absolutely necessary to store the setting information in the memory of the slave control circuit 40. It may be stored in a storage device separate from the slave control circuit 40 and read when needed.

While the present invention has been described based on the embodiment described above, the present invention is not limited to this embodiment and various modifications and application are of course possible within the scope of the main points of the present invention.

Moreover, inventions of various stages are contained in the embodiment described above, and various inventions can be extracted by appropriate combinations of a plurality of the constitutive requisites disclosed therein. For example, when the problems mentioned above can be solved even if some of the constitutive requisites are deleted from all the constitutive requisites disclosed in the embodiment, the configuration with the deleted constitute requisites can be extracted as an invention.

What is claimed is:

1. A control device comprising:
a controller configured to:
store first setting information representing a spatial relationship between:
a position and an orientation of a first target portion of a surgical tool attached to a slave arm; and
a position and an orientation of a second target portion of the surgical tool attached to the slave arm;
read a manipulation input value of the position and the orientation of the first target portion of the surgical tool, wherein the manipulation input value is input by a user from a remote control device;
correct the manipulation input value based on the first setting information to generate a corrected manipulation input value of the position and the orientation of the second target portion of the surgical tool; and
control one or more of the surgical tool and the slave arm based on the corrected manipulation input value.

2. The control device according to claim 1, wherein the control of one or more of the surgical tool and the slave arm based on the corrected manipulation input value comprises:
performing an inverse kinematics computation based on the corrected manipulation input value to calculate a drive quantity for one or more of the surgical tool and the slave arm needed to set the position and the orientation of the second target portion of the surgical tool; and
driving one or more of the surgical tool and the slave arm based on the drive quantity.

3. The control device according to claim 1 or 2, wherein the first setting information represents the spatial relationship between:
the position and the orientation of the first target portion of the surgical tool attached to the slave arm; and
the position and the orientation of the second target portion of the surgical tool attached to the slave arm, wherein the second target portion is determined based on a purpose of the surgical tool.

4. The control device according to claim 3,
wherein the surgical tool comprises a grasping part configured to grasp an object as the purpose of the surgical tool, and
wherein the first target portion is not part of the grasping part and the second target portion is part of the grasping part.

5. The control device according to claim 3,
wherein the surgical tool comprises an abutting part configured to abut on an object and to hold back the object as the purpose of the surgical tool, and
wherein the first target portion is not part of the abutting part and the second target portion is part of the abutting part.

6. The control device according to claim 3,
wherein the surgical tool comprises a cutting part configured to contact an object and to cut the object as the purpose of the surgical tool, and
wherein the first target portion is not part of the cutting part and the second target portion is part of the cutting part.

7. The control device according to claim 1, wherein the second target portion of the surgical tool is a portion of the surgical tool designated by the user.

8. The control device according to claim 1, wherein the controller is further configured to:
store a second setting information representing a spatial relationship between:
the position and the orientation of the first target portion of the surgical tool attached to the slave arm; and
a position and an orientation of a third target portion of the surgical tool attached to the slave arm,
wherein the second target portion of the surgical tool corresponds to a first usage location of the surgical tool and the third target portion of the surgical tool corresponds to a second usage location of the surgical tool,
select one of the first setting information and the second setting information based on a selection by the user;
correct the manipulation input value based on the one of the first setting information and the second setting information selected by the user to generate the corrected manipulation input value of a corresponding one of the position and the orientation of the second target portion of the surgical tool and the position and the orientation of the third target portion of the surgical tool; and
control one or more of the surgical tool and the slave arm based on the corrected manipulation input value.

9. The control device according to claim 1, further comprising:
a display configured to display the position and the orientation of the second target portion of the surgical tool.

10. The control device according to claim 9,
wherein the surgical tool further comprises an indicator configured to indicate the position and the orientation of the second target portion, and
wherein the display is configured to display the indicator.

11. A control method comprising:
storing first setting information representing a spatial relationship between:
a position and an orientation of a first target portion of a surgical tool attached to a slave arm; and a position and an orientation of a second target portion of the surgical tool attached to the slave arm;
reading a manipulation input value of the position and the orientation of the first target portion of the surgical tool, wherein the manipulation input value is input by a user from a remote control device;
correcting the manipulation input values based on the first setting information to generate a corrected manipulation input value of the position and the orientation of the second target portion of the surgical tool; and
controlling one or more of the surgical tool and the slave arm based on the corrected manipulation input value.

* * * * *